United States Patent
Englert et al.

[19]

[11] Patent Number: 6,139,337
[45] Date of Patent: Oct. 31, 2000

[54] ELASTOMERIC CONNECTION FOR COMPUTED TOMOGRAPHY SYSTEM

[75] Inventors: August O. Englert; Paul C. Schanen, both of Waukesha; Thomas R. Murray, Delafield; Brian D. Johnston, Oconomowoc; Darrell J. Miller, Mukwonago, all of Wis.

[73] Assignee: General Electric Company, Milwaukee, Wis.

[21] Appl. No.: 08/977,447

[22] Filed: Nov. 26, 1997

[51] Int. Cl.[7] .............................. H01R 4/58; H01R 12/00
[52] U.S. Cl. ................................................. 439/91; 439/66
[58] Field of Search .................................. 439/91, 94, 66, 439/67, 591

[56] References Cited

U.S. PATENT DOCUMENTS

| | | | |
|---|---|---|---|
| 4,075,527 | 2/1978 | Cummings | 313/93 |
| 4,181,856 | 1/1980 | Bone | 250/366 |
| 4,644,573 | 2/1987 | Palermo et al. | 378/15 |
| 5,199,882 | 4/1993 | Bates et al. | 439/67 |
| 5,757,878 | 5/1998 | Dobbs et al. | 378/19 |
| 5,795,162 | 8/1998 | Lambert | 439/63 |
| 5,846,094 | 12/1998 | Murray et al. | 439/91 |

*Primary Examiner*—Lincoln Donovan
*Assistant Examiner*—Chandrika Prasad
*Attorney, Agent, or Firm*—Armstrong Teasdale; Christian G. Cabou; Phyllis Y. Price

[57] ABSTRACT

An elastomeric connector apparatus for a computed tomography system is described. In one embodiment, the elastomeric connector apparatus electrically connects a detector module flexible cable to a data acquisition backplane. Flexible cable and backplane connector pads are electrically connected with an elastomeric connector. The elastomeric connector apparatus allows the low level analog outputs from the detector module photodiodes to be transmitted to the backplane without a large pin connector array.

26 Claims, 8 Drawing Sheets

ELASTOMERIC CONNECTION FOR COMPUTED TOMOGRAPHY SYSTEM

FIELD OF THE INVENTION

This invention relates generally to computed tomograph imaging and, more particularly, to coupling the electrical signals from the x-ray beam detection module to a backplane.

BACKGROUND OF THE INVENTION

In at least some computed tomograph (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodiodes adjacent the scintillator.

Multislice CT systems are used to obtain data for an increased number of slices during a scan. Known multislice systems typically include detectors generally known as 3-D detectors. With such 3-D detectors, a plurality of detector elements form separate channels.

Each detector module of the 3-D detector array has several times more output signals than known 1-D detector modules. The output lines of 1-D modules typically are connected to the CT system data acquisition system (DAS) using a pin connector or a printed wiring board mechanically connected to the DAS backplane. However, as the number of output lines becomes larger, so does the size of the array of the pin connector. As a result of the insertion force required with the larger pin connector array, the DAS backplane may be damaged.

Accordingly, it would be desirable to provide a connector apparatus that eliminates the need to mechanically couple a large pin connector array to the DAS backplane. It would also be desirable to provide such a connector apparatus that connects a high density of low level analog output lines to the DAS backplane.

SUMMARY OF THE INVENTION

These and other objects may be attained by an elastomeric connector that electrically connects the detector module output lines to the DAS backplane. Particularly, a detector module for a multislice system includes a plurality of detector elements and a flexible cable electrically connected, at a first end, to each element. The flexible cable second end is electrically coupled to the DAS backplane using the elastomeric connector so that an electrical connection is formed between the detector elements and the data acquisition system.

Particularly, the second end of each flexible cable wire is electrically connected to a connection pad. An identical connection pad is electrically connected to each line of the DAS backplane. The elastomeric connector includes a plurality of conductors for aligning with the connection pads, and the connector is positioned between the flex cable second end connection pad and the backplane connection pad so that electrical connections are made by the pads via the elastomeric connector. The elastomeric connector is then compressed and secured to the backplane by a housing. Specifically, as the housing is secured to the backplane, the elastomeric connector is compressed so that the elastomeric connector conductors are firmly held in electrical contact with the connection pads. As a result, an electrical connection is created between the detector module and the data acquisition system. Particularly, each photodiode output line is electrically connected to each DAS input line.

The above described elastomeric connector apparatus enables a large number of high density low level analog photodiode output lines to be electrically connected to the DAS backplane. In addition, the above described elastomeric connector apparatus eliminates the need to mechanically couple a pin connector array to the backplane.

DETAILED DESCRIPTION

Figure 1:
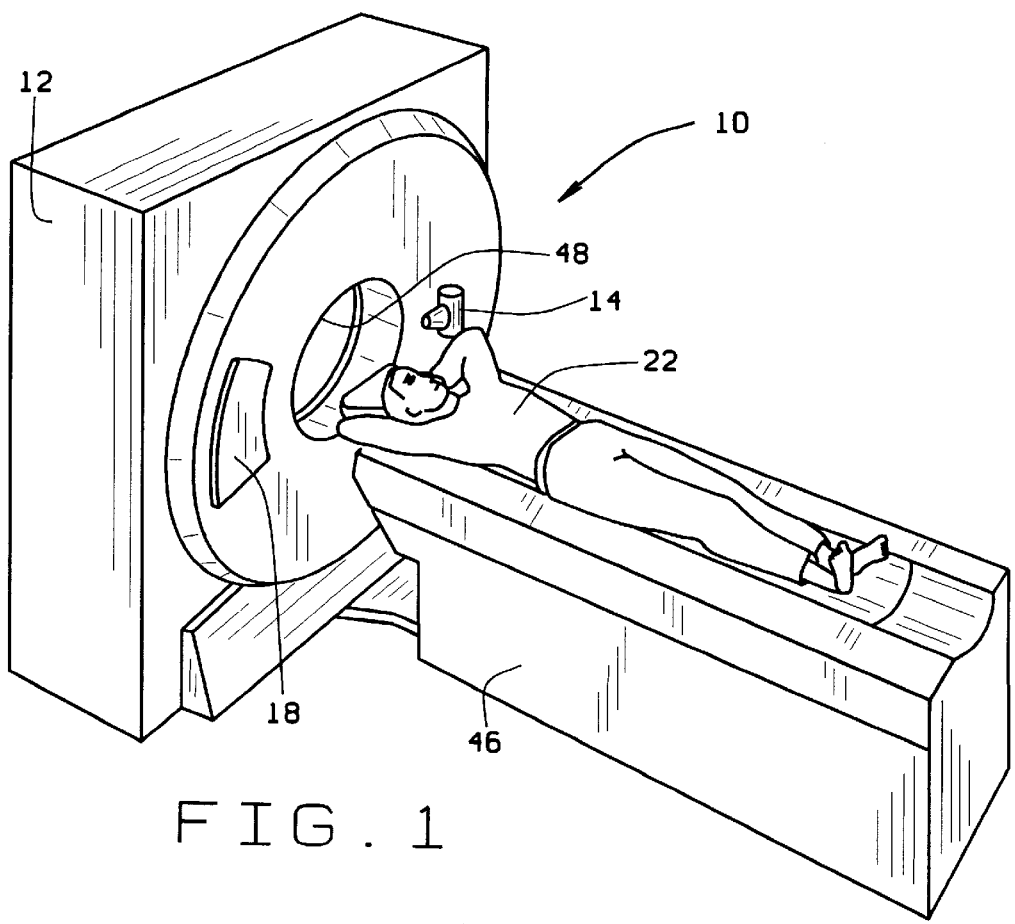
FIG. 1 is a pictorial view of a CT imaging system.
Figure 2:
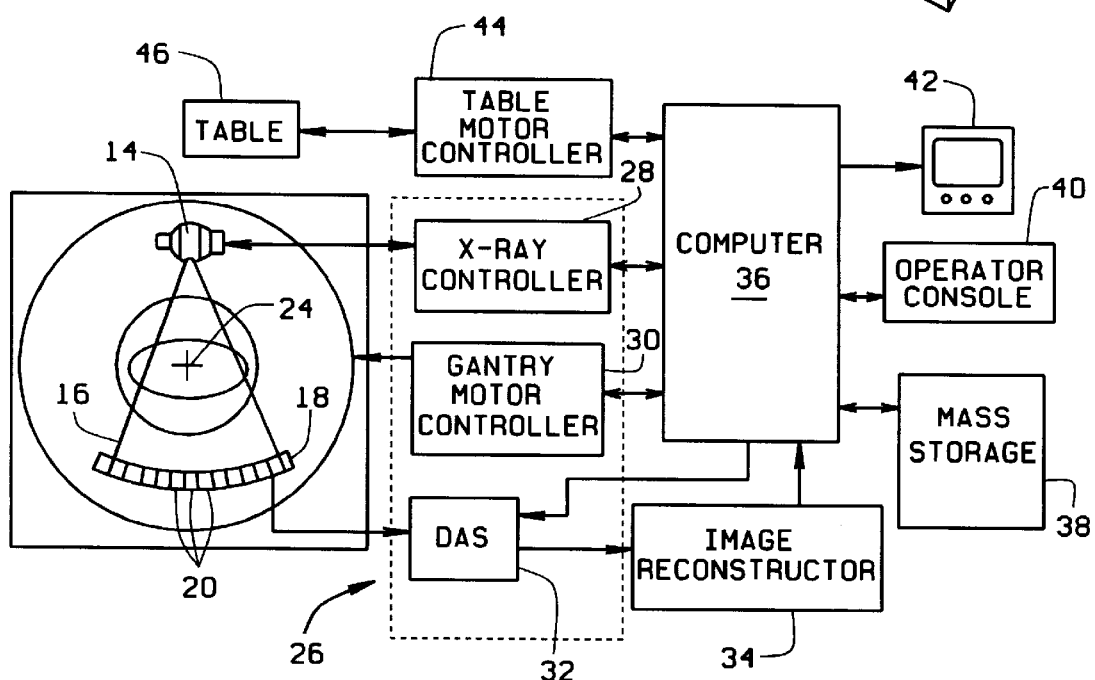
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector modules 20 which together sense the projected x-rays that pass through a medical patient 22. Each detector module 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector modules 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through a gantry opening 48.

Figures 3, 4:
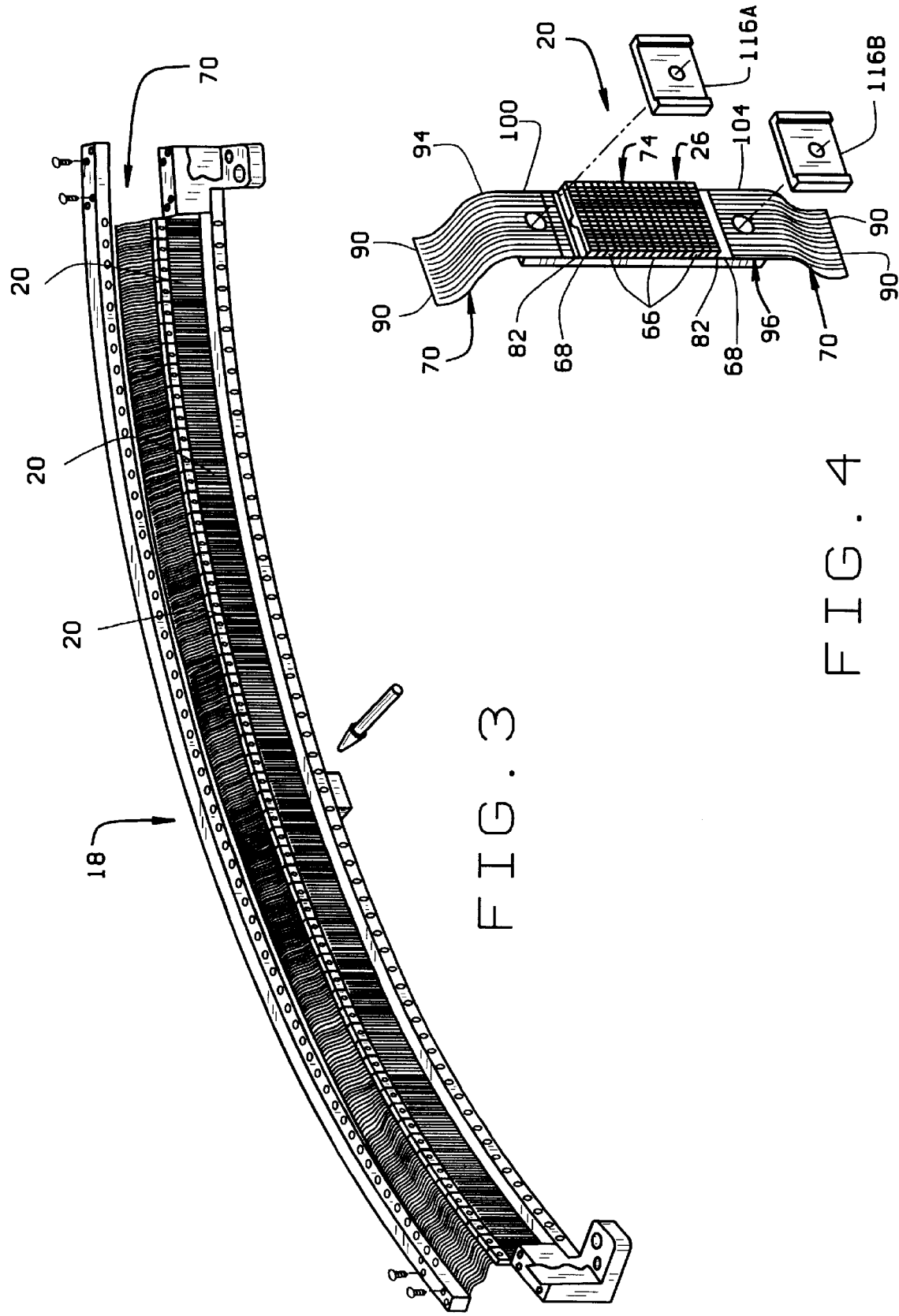
FIG. 3 is a perspective view of a CT system detector array.
FIG. 4 is a perspective view of a detector module shown in FIG. 3.
Figure 5:
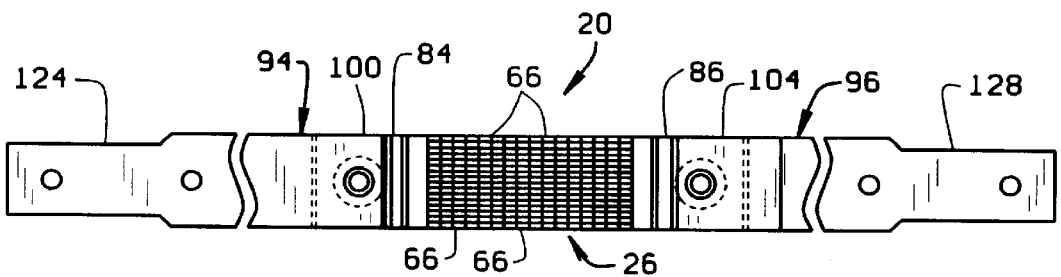
FIG. 5 is a top view of a detector module shown in FIG. 4.

As shown in FIGS. 3, 4 and 5, detector array 18 includes a plurality of detector modules 20. Each detector module includes an array of detector elements 26. Particularly, each x-ray detector module 20 includes a plurality of photodiodes 66, a semiconductor device 68, and at least one flexible electrical cable 70. Scintillators 74, as known in the art, are positioned over and adjacent photodiodes 66. Photodiodes 66 may be individual photodiodes or a multi-dimensional photodiode array. Photodiodes 66 are deposited, or formed on a substrate (not shown). Photodiodes 66 are optically coupled to scintillators 74 and have electrical output lines 82 for transmitting signals representative of the light output by scintillators 74. Each photodiode 66 produces a separate low level analog output signal that is a measurement of the beam attenuation for a specific element 26. Photodiode output lines 82 may, for example, be physically located on one side of module 20 or on a plurality of sides of module 20. As shown in FIG. 4, photodiode outputs 82 are located at opposing sides of the photodiode array.

Semiconductor device 68, in one embodiment, includes two semiconductor switches 84 and 86. Switches 84 and 86 each include a plurality of field effect transistors (FET) (not shown) arranged as a multidimensional array. Each FET includes an input line electrically connected to one of respective photodiode output lines 82, an output line, and a control line (not shown). FET output and control lines are electrically connected to flexible cable 70. Particularly, about one-half of photodiode output lines 82 are electrically connected to each FET input line of switch 84 with the other one-half of photodiode output lines 82 electrically connected to the FET input lines of switch 86.

Flexible electrical cable 70 includes a first end (not shown), a second end (not shown) and a plurality of electrical wires 90 traveling therebetween. Cable 70 may, for example, be two cables 94 and 96 having respective first ends 100 and 104 and respective second ends 124 and 128 or in an alternative embodiment, may include a single cable (not shown) having multiple first ends (not shown). In one embodiment, the FET output and control lines of switch 84 are connected to wires 90 of cable 94, and the FET output and control lines of switch 86 are connected to wires 90 of cable 96. Particularly, each FET output and control line is electrically connected to a wire 90 of respective cable first ends 100 and 104. Respective cable first ends 100 and 104 are held in firm electrical contact with the FETs by mounting brackets 116A and 116B.

Figure 6:
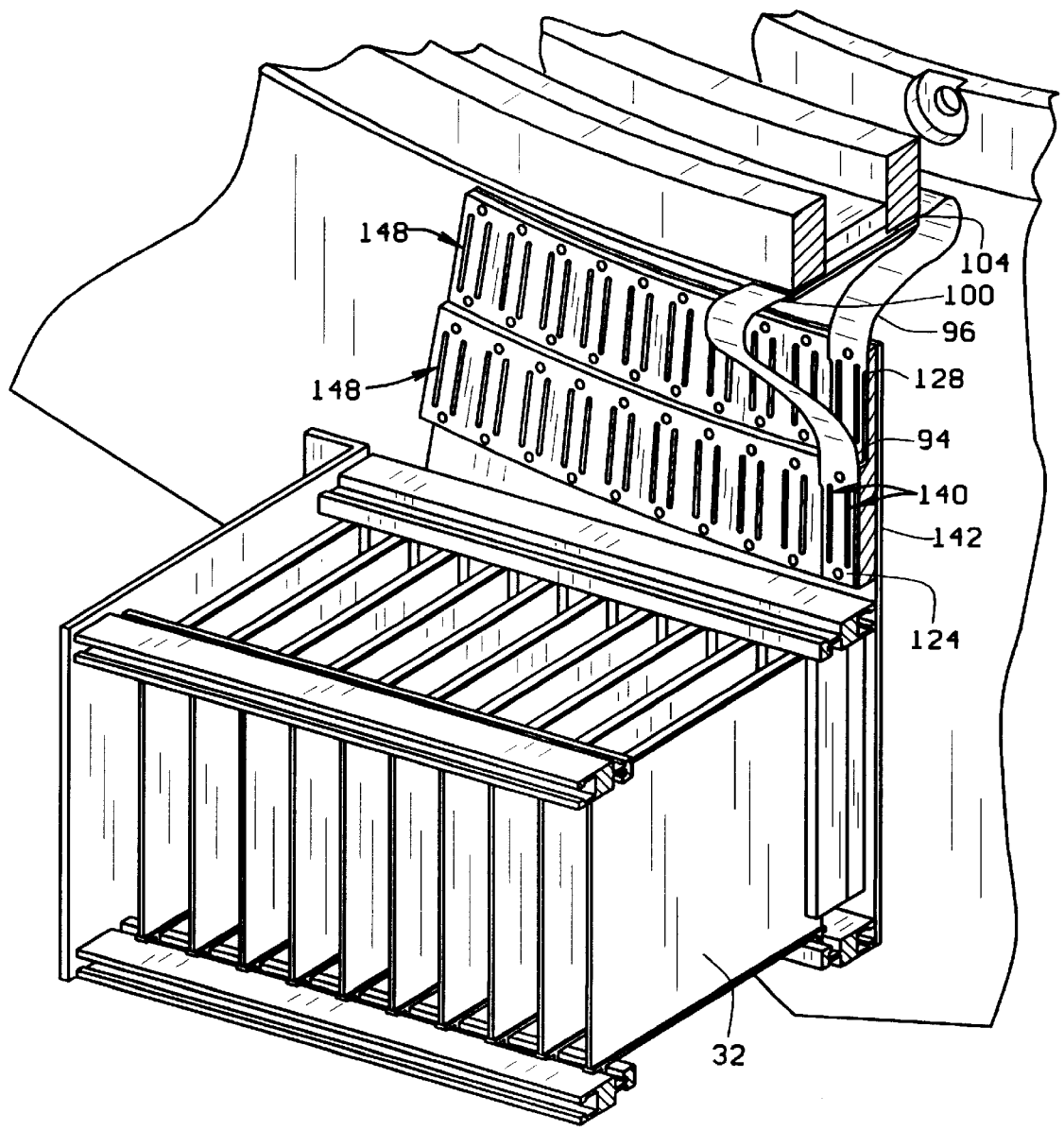
FIG. 6 is a perspective view of a detector module to data acquisition system interconnection prior to securing of the housing.
Figure 7:
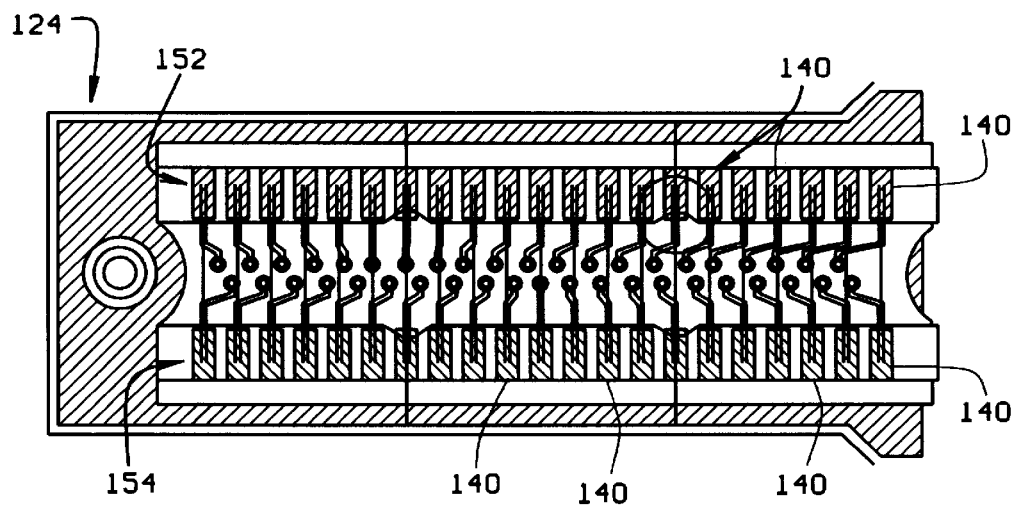
FIG. 7 is an enlarged top view of the flexible cable second end shown in FIG. 6.
Figure 8:
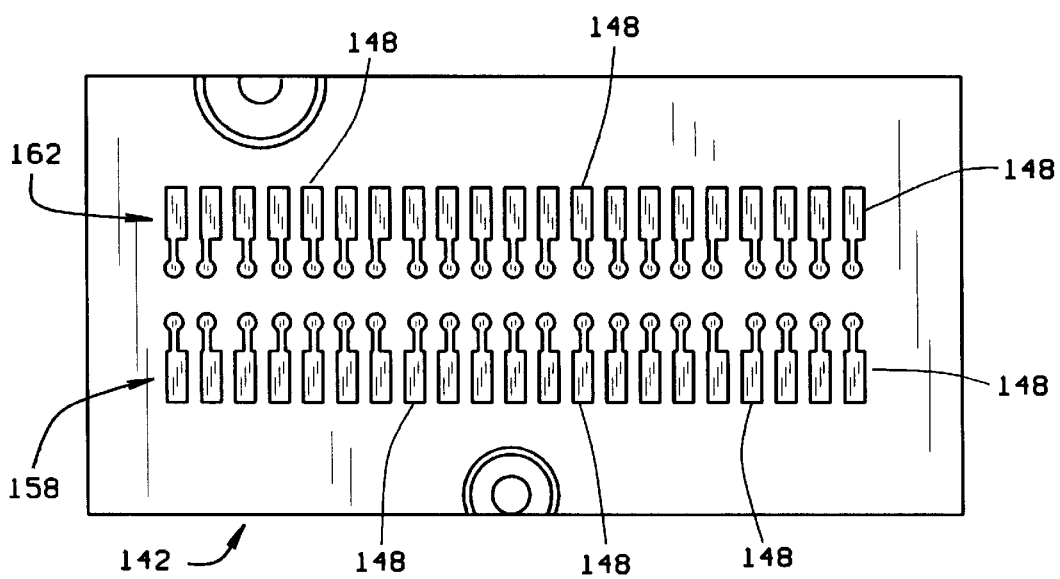
FIG. 8 is an enlarged top view of the backplane connection pads.

In one embodiment and referring to FIGS. 6, 7 and 8, cables 94 and 96 are identical. Referring specifically to cable 94, second end 124 includes a plurality of connection pads 140 arranged in a pattern. Each connection pad 140 is electrically connected to a wire 90 at cable second end 124. Cable second end 124 is electrically coupled to a DAS backplane 142 utilizing an elastomeric connector (not shown in FIGS. 6, 7, and 8). Backplane 142 includes a plurality of connection pads 148 arranged in a pattern identical to connection pads 140. Backplane connection pads 148 are electrically connected to DAS input and control lines (not shown). In one embodiment, connection pads 140 are arranged in a pattern having two parallel rows 152 and 154, connection pads 148 are similarly laid out having two parallel rows 158 and 162, and two elastomeric connectors (not shown) are utilized to electrically connect connection pads 140 and 148. Each elastomeric connector includes a plurality of conductors (not shown) aligning with the connection pads so that positioning the elastomeric connectors between cable second end 124 and backplane 142 electrically connects connection pads 140 and 148. Particularly, the first elastomeric connector is positioned between connection pad rows 152 and 158, and the second elastomeric connector is positioned between connection pad rows 154 and 162. Cable second end 124 is secured to backplane 142 with a housing (not shown). Cable 96 is connected to backplane 142 in a similar manner.

Figure 9:
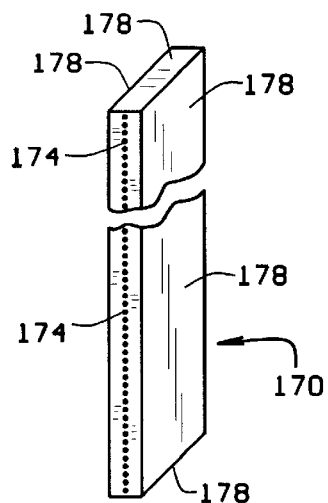
FIG. 9 is perspective view of an elastomeric connector.
Figure 10:
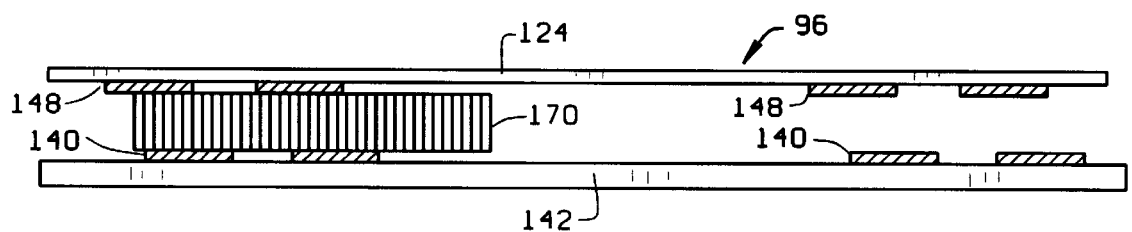
FIG. 10 is an enlarged side view of the flexible cable second end to data acquisition system interconnection shown in FIG. 6 with insulating material removed from the elastomeric connector.

Referring to FIG. 9, elastomeric connector 170 includes at least one conductor 174 surrounded on all sides by an insulating material 178. Ends of the elastomeric connector are not covered with insulating material 178 so that end tips of conductor 174 may make electrical connection with pads 140 and 148. In one embodiment, elastomeric connector 170 includes a plurality of gold plated brass conductors 174. Conductors 174 may be spaced so that a single conductor 174 makes electrical connection between each connection pad 140 and each connection pad 148. Alternatively, as shown in FIG. 10, conductors 174 may be spaced so that a plurality of conductors 174 make electrical connection between each connection pad 140 and each connection pad 148. Elastomeric conductors 174 are spaced so that an electrical connection between pads 140 and 148 is maintained by a plurality of conductors 174 despite misalignment of cable second end 124 and backplane 142. In one embodiment, for example, when pads 140 and 148 are perfectly aligned, nine conductors 174 electrically connect pads 140 and 148, whereas if pads 140 and 148 are misaligned, four conductors 174 electrically connect pads 140 and 148.

Figure 11:
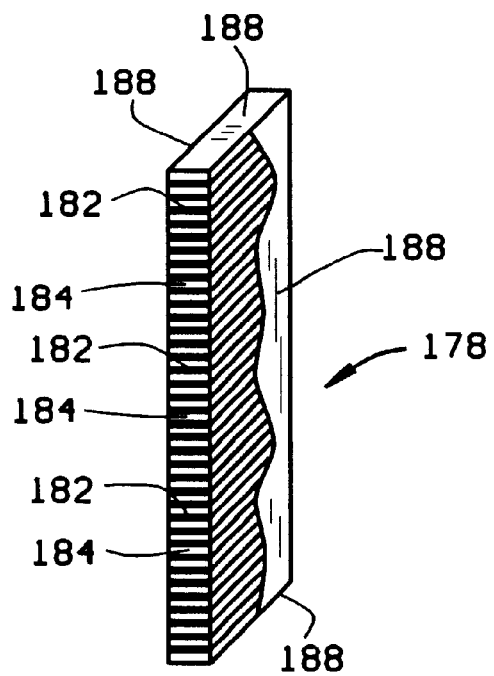
FIG. 11 is a perspective view of an alternative embodiment of the elastomeric connector with a portion of the insulating material removed.

As seen in FIGS. 9 and 10, end tips of conductors 174 are flush with ends of the elastomeric connector, and pads 140 and 148 are flush with the ends of the elastomeric connector. Pads 140 and 148 contact the end tips of conductors 174. In an alternative embodiment as shown in FIG. 11, an elastomeric connector 178 includes a plurality of conductor layers 182 of, for example, silver impregnated silicone. Layers 182 are separated from each other by insulation layers 184. Insulation material 188 fully insulates each layer 182. Each layer 182 makes electrical connection with a connection pad 140 and a connection pad 148 so that photodiode output lines 82 are coupled (e.g., via FETs and the flex cable) to the backplane inputs and the FET control lines are connected to the DAS control lines.

Figure 12:
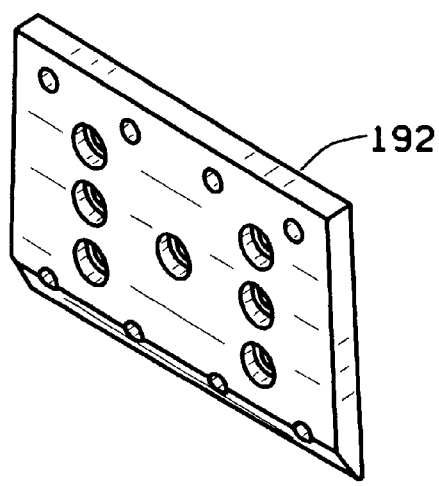
FIG. 12 is a perspective view of the housing for securing the connector to the backplane.
Figure 13:
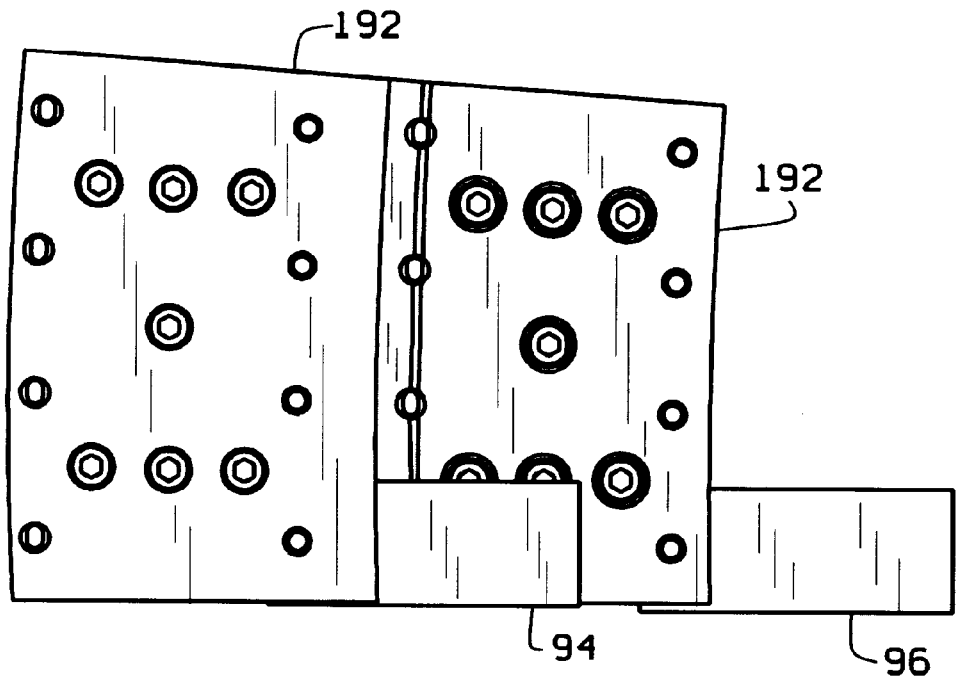
FIG. 13 is a top view of the housing secured to the backplane.
Figure 14:
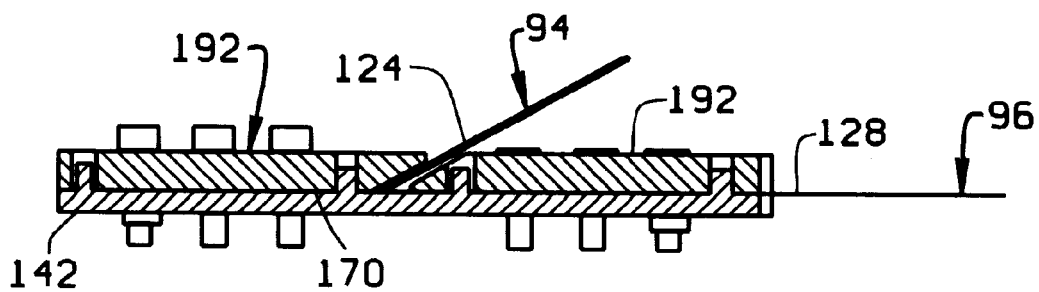
FIG. 14 is a side view of housing shown in FIG. 13.

In one embodiment and referring to FIGS. 12, 13 and 14, housing 192 fits over a plurality of cable second ends and is secured to backplane 142. Particularly, housing 192 compresses elastomeric connector 170 between flexible cable second end 124 and backplane 142 so that electrical connections are made by connection pads 140 (shown in FIG. 10) and 148 (shown in FIG. 10) via elastomeric conductors 174 (shown in FIG. 9). As a result, output lines 82 (shown in FIG. 4) are electrically coupled to the backplane input lines and the FET control lines are connected to the DAS control lines to configure detector module semiconductor switches 84 (shown in FIG. 5) and 86 (shown in FIG. 5). Housing 192 is secured to backplane 142 using at least one bolt (not shown).

Figure 15:
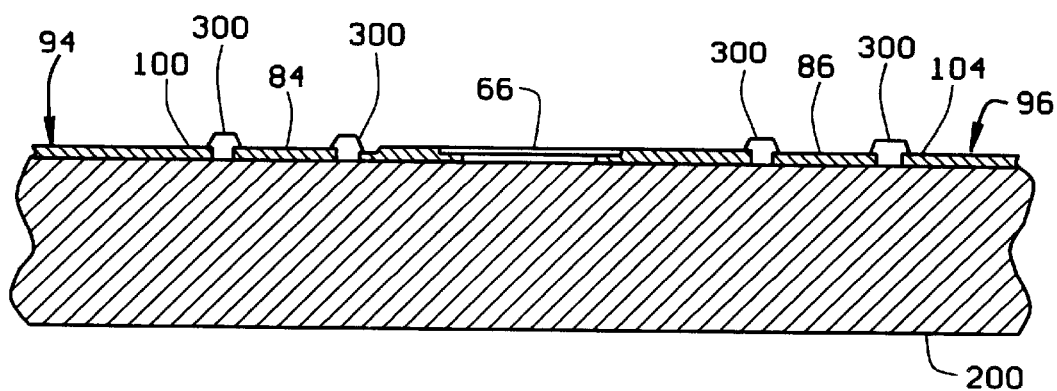
FIG. 15 is a side view of a portion of the detector module shown in FIG. 5.

As shown in FIG. 15, and with respect to detector module 20, photodiodes 66 and switches 84 and 86 are deposited, or formed, on substrate 200 so that photodiodes 66 are positioned adjacent and between switches 84 and 86. The FET input lines are electrically connected to photodiode output lines 82. Particularly, about one-half of photodiode outputs 82 are wire bonded to switch 84 input lines and about one-half of photodiode outputs 82 are wire bonded to switch 86 input lines so that an electrical path is created between each output line 82 and each FET input line. Switch input lines may be wire bonded to photodiode outputs 82 using various wire bonding techniques, including, for example, aluminum wire wedge bonding and gold wire ball bonding as known in the art. Wire bonds are generally identified as bonds 300.

Respective cable first ends 100 and 104 are positioned adjacent to respective switches 84 and 86 and coupled to substrate 200 using, for example, an adhesive (not shown). A portion of the FET output and control lines are then wire bonded to wires 90 of cable 94 and a portion of the FET output and control lines are wire bonded to wires 90 of cable 96 so that an electrical path is created between each FET output line and a wire 90 and each FET control line and a wire 90. Cable first ends 100 and 104 are maintained in place using mounting brackets 116A and 116B.

After mounting detector modules 20 into detector array 18, cable second ends 124 and 128 are coupled to DAS 32 so that an electrical path exists between the photodiode output lines 82 and the DAS inputs, and the FET control lines are electrically connected to the DAS outputs to enable semiconductor device FETs. Particularly, a first end of elastomeric connector 170 is positioned adjacent backplane 142 so that elastomeric conductors 174 are positioned adjacent connection pads 148. Flexible cable second end 124 is then positioned adjacent a second end of elastomeric connector 170 so that elastomeric conductors 174 are positioned adjacent connection pads 140. After positioning housing 192 over and adjacent cable second end 124, housing 192 is secured to backplane 142 until elastomeric connector 170 is compressed so that elastomeric conductors 174 are electrically connected to cable second end connection pads 140 and backplane connection pads 148.

The above described elastomeric connector apparatus may be utilized to complete various types of electrical connections. For example, two flexible electrical cables may be electrically coupled utilizing the elastomeric connector apparatus. Particularly, the ends of the cables would include a plurality of connection pads, and the elastomeric connector (not shown) would include a plurality of conductors for electrically connecting the respective first and second cable connection pads.

A coupling having a lower portion and an upper portion could be used to secure the first and second cables and compress the elastomeric connector so that the elastomeric connector conductors are electrically connected to the respective cable connection pads.

Particularly, the first and second cables are electrically connected by securing the elastomeric connector between the cable second ends. Initially, the first cable first end is positioned in the coupling lower portion. After placing the elastomeric connector in the coupling adjacent the first cable connection pads, the second cable first end is positioned adjacent to the elastomeric connector so that the second cable connection pads are adjacent to the elastomeric connector. The coupling upper portion is then positioned adjacent the second cable second end and secured to the coupling lower portion so that the elastomeric connector is compressed. As a result of the compression, the elastomeric connector conductors are electrically connected to the respective first and second cable connection pads so that a signal path exists between the first cable and the second cable. Additionally, various other electrical connections can be completed using the elastomeric connector, for example, connecting a flexible cable and a printed wiring board, or connecting a flexible cable to a silicon device, such as a photodiode.

The above described detector module enables a large number of high density low level analog photodiode output lines to be electrically connected to the backplane. Additionally, as a result of the elastomeric connection of the flexible cable, a large pin connector array is not required to be connected to the backplane. Eliminating the connection of the pin connector avoids subjecting the detector module to the insertion force of the pin connector and the potential damage associated with making such a connection.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. An elastomeric connector apparatus for a computed tomography machine, said connector apparatus comprising:
a detector module comprising at least one flexible cable; said flexible cable comprising a first end and a second end, said first end electrically connected to said detector module;
a backplane; and
at least one elastomeric connector with a front end, a back end, and a conductor having a first end tip flush with said front end and a second end tip flush with said back end, said front end having said first end tip of said conductor electrically connected to and contacting said second end of said flexible electrical cable, and said back end having said second end tip of said conductor electrically connected to and contacting said backplane.

2. An elastomeric connector apparatus in accordance with claim 1 wherein said second end of said flexible cable and an input of said backplane each comprise a connection pad, and wherein said connection pads are configured to electrically couple to said elastomeric connector.

3. An elastomeric connector apparatus in accordance with claim 1 wherein said elastomeric connector comprises a silver impregnated silicone layer conductor.

4. An elastomeric connector apparatus in accordance with claim 1 wherein said elastomeric connector comprises a gold plated brass or nickel conductor.

5. An elastomeric connector apparatus in accordance with claim 1 wherein said backplane comprises a plurality of inputs, and wherein said flexible electrical cable comprises a plurality of wires.

6. An elastomeric connector apparatus in accordance with claim 5 wherein said elastomeric connector comprises a plurality of conductors configured to electrically connect each of said wires to each of said inputs.

7. An elastomeric connector apparatus in accordance with claim 6 wherein elastomeric connector conductors are gold plated brass.

8. An elastomeric connector apparatus in accordance with claim 5 wherein said elastomeric connector comprises a plurality of silver impregnated silicone layers.

9. An elastomeric connector apparatus in accordance with claim 5 comprising two elastomeric connectors, wherein each said elastomeric connector is configured to electrically connect a portion of said inputs to a portion of said wires.

10. An elastomeric connector apparatus in accordance with claim 9 wherein each said elastomeric connector comprises a plurality of conductors.

11. An elastomeric connector apparatus in accordance with claim 10 wherein said conductors are gold plated brass.

12. An elastomeric connector apparatus in accordance with claim 9 wherein each said elastomeric connector comprises a plurality of silver impregnated silicone layers.

13. An elastomeric connector apparatus in accordance with claim 1 further comprising a housing configured to compress said elastomeric connector between said flexible cable and said backplane.

14. A method for coupling low level analog signals within a computed tomography machine utilizing an elastomeric connector apparatus, the computed tomography machine including a scintillator, a photodiode optically coupled to the scintillator, and a switch electrically coupled to an output of said photodiode, said elastomeric connector apparatus including a detector module having at least one flexible electrical cable, and a backplane, said method comprising the steps of:

positioning a first end of the flexible electrical cable adjacent an output of the switch;

bonding the first end of the cable to the output of the switch;

positioning a back end of an elastomeric connector adjacent an input of the backplane, the elastomeric connector having a conductor surrounded on all sides by an insulating material except for end tips of said conductors at a front end of the elastomeric connector and at the back end of the elastomeric connector;

positioning the front end of the flexible electrical cable adjacent a back end of the elastomeric connector; and securing a cable second end to the backplane.

15. A method in accordance with claim 14 wherein securing the cable second end to the backplane comprises the step of compressing the elastomeric connector until the elastomeric connector is electrically connected to the cable second end and the backplane input.

16. A method in accordance with claim 14 wherein the elastomeric connector includes a plurality of conductors having end tips, wherein each of the backplane inputs includes a connector pad, and wherein positioning a back end of the elastomeric connector adjacent an input of the backplane comprises the step of positioning the end tips of the back end elastomeric connector conductors adjacent the backplane input connector pads.

17. A method in accordance with claim 14 wherein the flexible electrical cable includes a plurality of wires, each wire electrically connected to a connector pad located at the second end of the flexible cable, and wherein positioning the second end of the flexible electrical cable adjacent a front end of the elastomeric connector comprises the step of positioning the front end elastomeric connector conductors adjacent the flexible electrical cable connector pads.

18. A method in accordance with claim 17 wherein the elastomeric connector apparatus further comprises a housing, wherein compressing the elastomeric connector until the elastomeric connector is electrically connected to the cable second end and the backplane input comprises the step of securing the housing to the backplane.

19. Apparatus comprising:

a first flexible electrical cable having a first end having a plurality of connection pads;

a second flexible electrical cable having a first end having a plurality of connection pads; and an elastomeric connector positioned adjacent the connection pads of each of the first and the second flexible electrical cables electrically connecting low level analog signals from said first cable first end to said second cable first end.

20. Apparatus in accordance with claim 19 wherein said elastomeric connector comprises a plurality of conductors.

21. An elastomeric connector apparatus in accordance with claim 1 wherein said elastomeric connector is surrounded on all sides by an insulating material except at said front end and at said back end.

22. An elastomeric connector apparatus in accordance with claim 21 wherein said elastomeric connector has a plurality of conductors, wherein said first end tips of said conductors and said second end tips of said conductors are flush with said front end of said elastomeric connector and said back end of said elastomeric connector, respectively.

23. An elastomeric connector apparatus in accordance with claim 2 wherein said elastomeric connector comprises a plurality of conductors each having a first end tip and a second end tip, and wherein said first end tips of said conductors and said second end tips of said conductors are spaced so that an electrical connection between said connection pad of said flexible cable and said connection pad of said backplane is maintained by a plurality of conductors of said elastomeric connector despite misalignment of said cable second end and said backplane.

24. Apparatus in accordance with claim 19 wherein said elastomeric connector is surrounded on all sides by an insulating material except at a front end and at a back end.

25. Apparatus in accordance with claim 24 wherein said elastomeric connector comprises a plurality of conductors having first end tips flush with said front end and second end tips flush with said back end.

26. A method in accordance with claim 16 wherein the end tips of the back end elastomeric connector conductors are flush with the back end of the elastomeric connector, and positioning the end tips of the back end elastomeric connector conductors adjacent the backplane input connector pads comprises the step of positioning the backplane input connector pads flush with the back end of the elastomeric connector.

* * * * *